United States Patent
Weinmann et al.

(10) Patent No.: US 7,462,718 B2
(45) Date of Patent: Dec. 9, 2008

(54) PROCESS FOR THE PRODUCTION OF HIGH-PURITY RAC-1-{4-[2-HYDROXY-3-(5-QUINOLYLOXY) PROPYL]-PIPERAZIN-1-YL}-2,2-DIPHENYLETHAN-1-ONE FUMARATE AND HIGH-PURITY RAC-1-{4-[2-HYDROXY-3-(5-QUINOLYLOXY) PROPYL]PIPERAZIN-1-YL}-2,2-DIPHENYLETHAN-1-ONE FUMARATE

(75) Inventors: Hilmar Weinmann, Glienecke (DE); Matthias Schneider, Berlin (DE); Michael Gottfried, Berlin (DE)

(73) Assignee: Schering AG, Berlin (DE)

( * ) Notice: Subject to any disclaimer, the term of this patent is extended or adjusted under 35 U.S.C. 154(b) by 461 days.

(21) Appl. No.: 10/839,713

(22) Filed: May 6, 2004

(65) Prior Publication Data

US 2005/0014945 A1    Jan. 20, 2005

Related U.S. Application Data

(60) Provisional application No. 60/469,008, filed on May 9, 2003.

(30) Foreign Application Priority Data

May 6, 2003    (DE)    ................ 103 21 255

(51) Int. Cl.
    *C07D 295/023* (2006.01)
(52) U.S. Cl. .................................... 544/386
(58) Field of Classification Search ............ 544/366
    See application file for complete search history.

(56) References Cited

FOREIGN PATENT DOCUMENTS

| EP | 0363212 A2 | 4/1990 |
|----|-----------|--------|
| EP | 0575890 A1 | 12/1993 |
| JP | 2000281653 A | 10/2000 |

OTHER PUBLICATIONS

Patent Abstracts of Japan, 2000, No. 13, Feb. 5, 2001, JP 2000 281653A (Mitsui Chemicals Inc.).

Tsuneji Suzuki et al. "Structure Activity Relationship of Newly Synthesized Quinolione Derivatives for Reversal of Multidrug Resistance in Cancer" Journal of Medicinal Chemistry, American Chemical Society, 40, 13, 1997, p. 2047-2052, ISSN 0022-2623.

*Primary Examiner*—Johann Richter
*Assistant Examiner*—Ebenezer Sackey
(74) *Attorney, Agent, or Firm*—Miller, White, Zelano, Branigan, P.C.

(57) ABSTRACT

A process for the production of high-purity rac-1-{4-[2-hydroxy-3-(5-quinolyloxy)propyl]-piperazin-1-yl}-2,2-diphenylethan-1-one fumarate as well as rac-1-{4-[2-hydroxy-3-(5-quinolyloxy)propyl]piperazin-1-yl}-2,2-diphenylethan-1-one fumarate at a purity of at least 98.55% is described.

15 Claims, No Drawings

PROCESS FOR THE PRODUCTION OF HIGH-PURITY RAC-1-{4-[2-HYDROXY-3-(5-QUINOLYLOXY)PROPYL]-PIPERAZIN-1-YL}-2,2-DIPHENYLETHAN-1-ONE FUMARATE AND HIGH-PURITY RAC-1-{4-[2-HYDROXY-3-(5-QUINOLYLOXY)PROPYL]PIPERAZIN-1-YL}-2,2-DIPHENYLETHAN-1-ONE FUMARATE

This application claims the benefit of the filing date of U.S. Provisional Application Ser. No. 60/469,008 filed May 9, 2003.

The invention relates to a process for the production of high-purity rac-1-{4-[2-hydroxy-3-(5-quinolyloxy)propyl]-piperazin-1-yl}-2,2-diphenylethan-1-one fumarate as well as rac-1-{4-[2-hydroxy-3-(5-quinolyloxy)propyl]piperazin-1-yl}-2,2-diphenylethan-1-one fumarate at a purity of at least 99.55%.

The multidrug-resistance modulator rac-1-{4-[2-hydroxy-3-(5-quinolyloxy)propyl]-piperazin-1-yl}-2,2-diphenylethan-1-one fumarate, its production and use as carcinostatic pharmaceutical agent in addition to other derivatives of this compound is described in EP 575890.

According to the process for the production of pure rac-1-{4-[2-hydroxy-3-(5-quinolyloxy)propyl]-piperazin-1-yl}-2,2-diphenylethan-1-one fumarate that is described in EP 575890, the free base 5-[3-{4-(2,2-diphenylacetyl)piperazin-1-yl}-2-hydroxypropoxy]quinoline is first isolated as a crude product by coupling the two components epoxiline (B) (5-(2,3-epoxypropoxy)-quinoline) and diphenepiperazide (C) (N-(2,2-diphenylacetyl)piperazine). This reaction contains two partial stages. First, the epoxylate is reacted with hydroxyquinoline (A). In the second step, the epoxiline (B) (5-(2,3-epoxypropoxy)-quinoline) is opened by diphenepiperazide (C)(N-(2,2-diphenylacetyl)piperazine); it produces the secondary alcohol (D). This reaction takes place in ethanol; water catalyzes the reaction. The working-up/isolation is then carried out by precipitation from acetone/water and drying in a vacuum at 60° C.

The total reaction is produced from the diagram below:

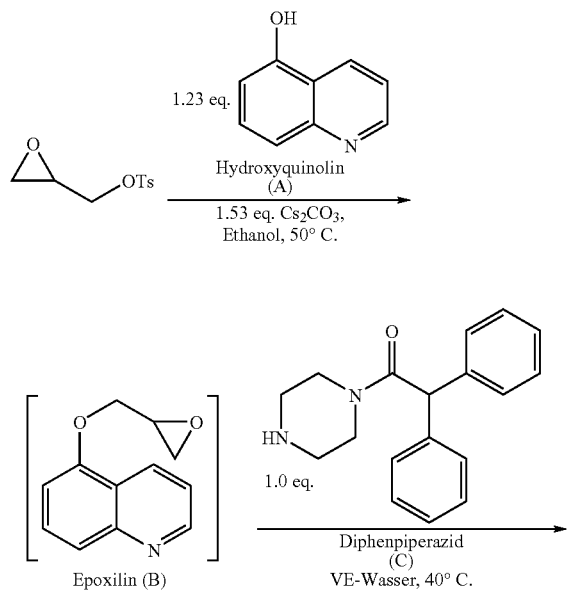

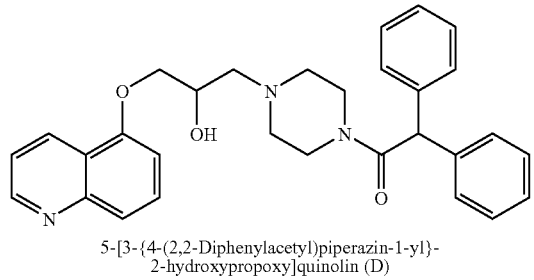

5-[3-{4-(2,2-Diphenylacetyl)piperazin-1-yl}-2-hydroxypropoxy]quinolin (D)

[Key:]
Hydroxyquinolin = hydroxyquinoline
Epoxilin = epoxiline
Diphenpiperazid = diphenepiperazide
VE-Wasser = VE water
-quinolin = -quinoline In the next step, a very expensive purification process follows the isolation of the free base, which still contains many contaminants (purity of the crude product typically about 80%). After the free base is treated with activated carbon and after the fumarate is formed in methanol, the free base is produced again for purification by treatment with dilute sodium hydroxide solution. Then, as a last step, repeated fumarate formation is carried out. The two fumarate formations are identical as far as processing is concerned and are distinguished only by the batch size (T. Suzuki et al., J. Med. Chem. (1997) 40, 2047) (JP 2000281653). Starting from the free base crude product, the typical laboratory yield for this purification sequence is 45% of theory.

In this case, not only is the low yield (over 50% loss in the final stage) disadvantageous in this process, but also the expensive technical execution, which binds many operational capacities and thus produces elevated costs. Especially disadvantageous in this case is the extremely poor filterability of the free base, which must be partially filter-dried over several weeks.

Despite the high expense as far as processing is concerned, the extremely high purification requirements of rac-1-{4-[2-hydroxy-3-(5-quinolyloxy)propyl]piperazin-1-yl}-2,2-diphenylethan-1-one fumarate are not always achieved in a completely satisfactory manner according to this known process.

Also, the process that is described in EP 575 890 does not provide any reasonable results in the scale-up.

The following diagram provides an overview of the individual reactions:

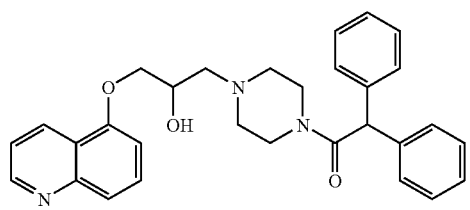

freie Base des
5-[3-(4-(2,2-Diphenylacetyl)piperazin-
1-yl-2-hydroxypropoxy)quinolins
(D)

2.52 eq. Fumarsäure,
Aktivkohle
Methanol, 60° C., 0° C.

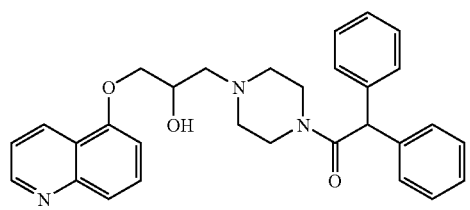

1.5•HOOC COOH

Fumarat des
5-[3-(4-(2,2-Diphenylacetyl)piperazin-
1-yl-2-hydroxypropoxy)quinolins
(E)

3.7 eq. NaOH
Methanol/Wasser
60° C.

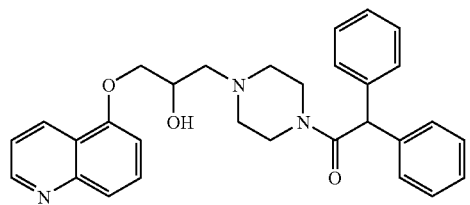

freie gereinigte Base des
5-[3-(4-(2,2-Diphenylacetyl)piperazin-
1-yl-2-hydroxypropoxy)quinolins
(D)

2.52 eq. Fumarsäure,
Aktivkohle
Methanol, 60° C., 0° C.

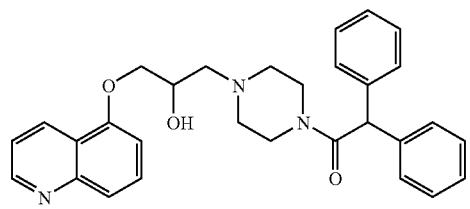

1.5•HOOC COOH reines Fumarat des
5-[3-(4-(2,2-Diphenylacetyl)piperazin-
1-yl-2-hydroxypropoxy)quinolins
(E)

[Key:]
freie Base des = free base of
-quinolins = quinoline
Fumarsäure = fumaric acid
Aktivkohle = activated carbon
Fumarat des = fumarate of
Wasser = water
freie gereinigte Base des = free purified base of
reines Fumarat des = pure fumarate of It has now been found that with the process according to the invention, these known drawbacks can be overcome. In the process according to the invention, the epoxiline (B) and diphenepiperazide (C) are first also coupled by opening the epoxide. Then, however, not the free base (D), but rather, after the solid fumaric acid is added directly, fumarate salt (E) is isolated as a crude product.

The subject of the application is thus a process for the production of high-purity rac-1-{4-[2-hydroxy-3-(5-quinolyloxy)propyl]-piperazin-1-yl}-2,2-diphenylethan-1-one fumarate, which is characterized in that first a) an epoxytosylate of structure I (I)

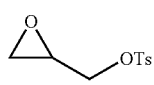

can be reacted with b) 5-hydroxyquinoline (II)

(II)

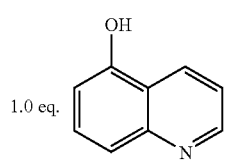

1.0 eq.

and cesium carbonate in a suitable solvent and at a suitable temperature to form the 5-(2,3-epoxypropoxy)-quinoline of formula III (III)

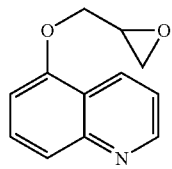

and then the 5-(2,3-epoxypropoxy)-quinoline of formula III c) is reacted with N-(2,2-diphenylacetyl)piperazine of formula IV

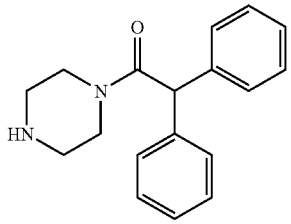

(IV)

in a suitable solvent and at a suitable temperature with the subsequent addition of solid fumaric acid to form crude rac-1-{4-[2-hydroxy-3-(5-quinolyloxy)propyl]-piperazin-1-yl}-2,2-diphenylethan-1-one fumarate of formula V

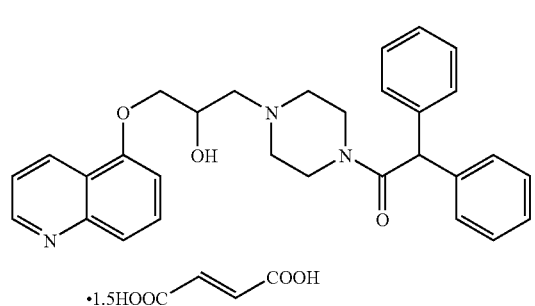

(V)

and then d) the thus formed crude rac-1-{4-[2-hydroxy-3-(5-quinolyloxy)propyl]-piperazin-1-yl}-2,2-diphenylethan-1-one fumarate (V) is isolated and is dissolved in a solvent mixture that consists of methanol and methylene chloride, is treated with activated carbon, and then is filtered through a pressure filter with silica gel as a column material, and the thus obtained pure rac-1-{4-[2-hydroxy-3-(5-quinolyloxy)propyl]-piperazin-1-yl}-2,2-diphenylethan-1-one fumarate (V) is crystallized from a suitable alcohol.

The reaction is preferably carried out in a temperature range of 35 to 60° C.

Suitable solvents are, e.g., ketones, such as acetone, methyl-isobutylketone, etc., alcohols, such as methanol, ethanol, isopropanol etc., amides, such as dimethylformamide, dimethylacetamide, N-methyl-pyrrolidone, etc.

In comparison to the known process, the crude rac-1-{4-[2-hydroxy-3-(5-quinolyloxy)propyl]-piperazin-1-yl}-2,2-diphenylethan-1-one of process stage c) that is isolated via the process according to the invention already exhibits a dramatically increased purity of 90-96%.

The purification step that is included in process stage d) is preferably performed in a solvent mixture that consists of MeOH/MeCl$_2$ at a ratio of 3:7, v:v.

Norit SX Plus is preferably used as activated carbon.

The amount of silica gel is preferably 3× the amount relative to the starting material.

The temperature in the crystallization in process stage (d) is preferably 0° C.

The typical laboratory yield for purification step (d) is 84% of theory.

PRODUCTION EXAMPLE

Production of rac-1-{4-[2-Hydroxy-3-(5-quinolyloxy)propyl]-piperazin-1-yl}-2,2-diphenylethan-1-one fumarate A) Under nitrogen, 44.2 g of 5-hydroxy-quinoline and 151.9 g of cesium carbonate are added together with 560 ml of acetone at room temperature and stirred for 30 minutes at a bath temperature of 60° C.

At an internal temperature of 50.degree. C., 73.0 g of epoxytosylate, dissolved in 153.3 g of dichloromethane, is added. Stirring is continued for two hours at 50.degree. C. The batch is filtered at 50.degree. C. The filter residue (inorganic salts) is rewashed with 560 ml of acetone heated to 50.degree. C. Then, 85.4 g of N-(2,2-diphenyl-acetyl)piperazine is added, and it is concentrated by evaporation at a bath temperature of 40.degree. C. in a vacuum to 374 g of final weight. Then, 374 g of VE-water is added, and it is stirred for 2 hours at 40.degree. C. Then, 255 g of acetone and 201 g of VE-water are added. The batch is cooled to room temperature, and 89.1 g of fumaric acid in solid form is added. It is stirred for 60 minutes at a bath temperature of 60.degree. C. and then stirred for 2 hours at 0.degree. C. Then, the solid is suctioned off and rewashed with 150 ml of ice-cold methanol. The filter residue is dried at 60.degree. C. in a vacuum.

Yield: 65-85% of theory

B) 56.0 g of the thus produced rac-1-{4-[2-hydroxy-3-(5-quinolyloxy)propyl]-piperazin-1-yl}-2,2-diphenylethan-1-one fumarate was mixed under nitrogen and at room temperature with 5.6 g of activated carbon, Norit SX plus, 672 ml of methanol and 1008 ml of dichloromethane. The suspension that is produced is heated at a bath temperature of 75° C. to reflux temperature and is kept at reflux for 30 minutes. At an internal temperature of 40° C., rac-1-{4-[2-hydroxy-3-(5-quinolyloxy)propyl]-piperazin-1-yl}-2,2-diphenylethan-1-one fumarate goes into solution. Then, the batch is hot-filtered through 300% silica gel, and the silica gel is rewashed with 560 ml of a mixture that consists of 168 ml of methanol and 392 ml of dichloromethane at room temperature RT. The solution is concentrated by evaporation at a bath temperature of 40° C. and an initial vacuum of 400 mbar to a final volume of 517 ml. The final vacuum is 350 mbar. The distilled volume corresponds approximately to the volume difference (about 1.71). 404 ml of methanol is added, such that a final volume of 921 ml is reached. The solution is cooled to 0° C., whereby the product precipitates. The suspension that is produced is stirred for 2 hours at 0° C. and then filtered through a paper filter. The filter residue is washed with 56.0 ml of ice-cold methanol. The filter residue is dried at 60° C. and dried in a vacuum at 100 mbar for 10 hours.

Yield (uncorr.): 47.29 g ( 84.45% of the experiment)

Purity: 99.65% (HPLC, 100% method)

| Comparison of the Prurification Process that is Known in the Literature with the Purification Process According to the Invention | | |
|---|---|---|
| | Purification Process that is Known in the Literature | Purification Process According to the Invention |
| Total Yield of the Synthesis over All Stages | 28% of Theory | 43% of Theory |
| Purity (HPLC, 100% Method) | 98.54%, several VU over 0.1% | 99.55-99.89%, no VU over 0.1% |

| Comparison of the Prurification Process that is Known in the Literature with the Purification Process According to the Invention | |
|---|---|
| Purification Process that is Known in the Literature | Purification Process According to the Invention |
| Technical Expense | High, several intermediate isolations are necessary, also extremely poor filterability | Significantly reduced time requirement in operation due to greater ease of technical implementation. |

VU = contaminants

From the results, it can be seen that the total yield of rac-1-{4-[2-hydroxy-3-(5-quinolyloxy)propyl]-piperazin-1-yl}-2,2-diphenylethan-1-one fumarate (V) can be increased by more than 50%.

From the results, it can also be seen that with the process according to the invention, the necessary extremely high purities can be reached, by which the technical expense could be greatly reduced at the same time. It can also be noted that contaminants (VU) 1-4, which are formed during the reaction, can be completely avoided.

A comparison of feedstocks, which had been produced according to the known process and according to the process of the invention, is indicated in the table below.

| Contaminant (VU) | Known Process | Process According to the Invention |
|---|---|---|
| VU 1 HOOC–CH=CH–COOMe | 0.80% | n.d. |
| VU 2 [structure] | 0.44% | n.d. |
| VU 3 [structure] | 0.08% | n.d. |

| Contaminant (VU) | Known Process | Process According to the Invention |
|---|---|---|
| VU 4 | 0.11% | n.d. |
| VU 5 Unknown Structure | <0.1% *) | 0.01 *) |
| VU 6 | <0.1% *) | 0.02 *) |
| Purity | 98.54% | 99.84% | n.d. = not detectable, since under the detection limit
*) Dependent on the purity of the commercially available products (educts): if contained in the educt at <0.2%.

Additional contaminants, which are formed during synthesis and also are removed effectively by the process according to the invention:

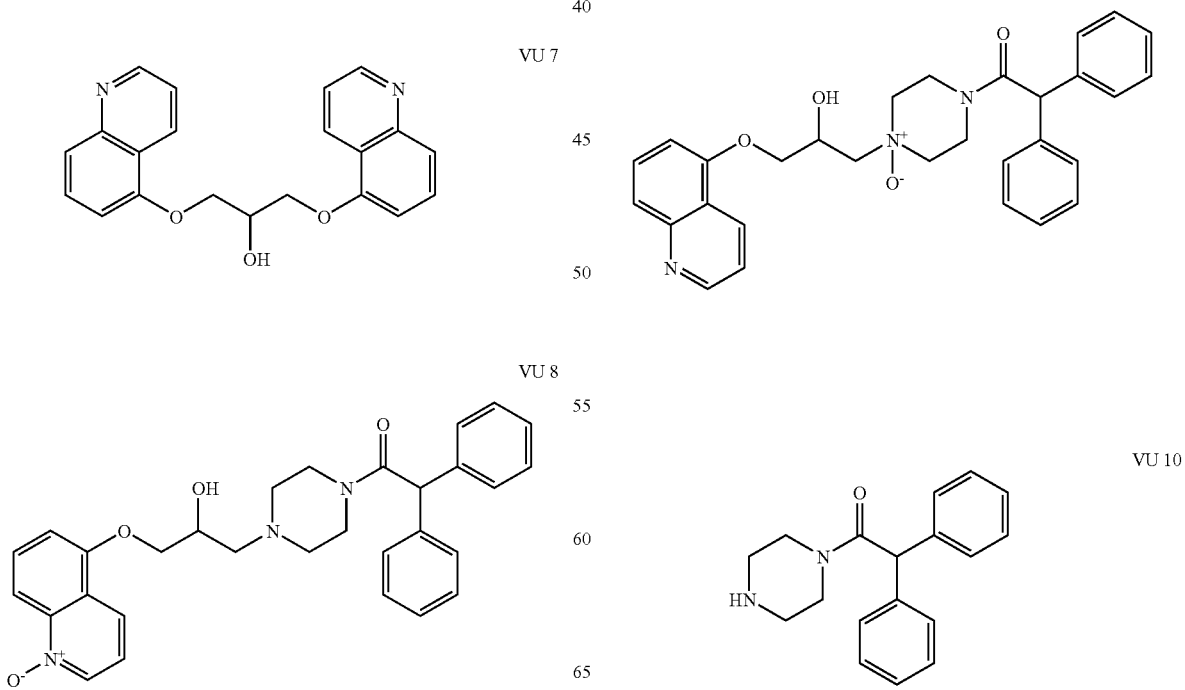

VU 11

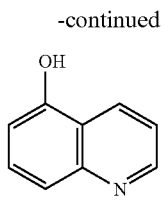

The subject of this invention is thus also rac-1-{4-[2-hydroxy-3-(5-quinolyloxy)propyl]-piperazin-1-yl}-2,2-diphenylethan-1-one fumarate at a purity of more than 98.54%.

In addition, a subject of this invention is also rac-1-{4-[2-hydroxy-3-(5-quinolyloxy)propyl]-piperazin-1-yl}-2,2-diphenylethan-1-one fumarate at a purity of at least 98.55%, especially at a purity of at least 99.55%, especially at a purity of at least 99.65% as well as at a purity of at least 99.84%.

The process according to the invention is suitable in particular for the production of rac-1-{4-[2-hydroxy-3-(5-quinolyloxy)propyl]-piperazin-1-yl}-2,2-diphenylethan-1-one fumarate on a process-technology scale. Thus, with this process, rac-1-{4-[2-hydroxy-3-(5-quinolyloxy)propyl]-piperazin-1-yl}-2,2-diphenylethan-1-one fumarate can be produced for the first time in amounts of more than 1000 g in the purity described.

A subject of this invention is also rac-1-{4-[2-hydroxy-3-(5-quinolyloxy)-propyl]-piperazin-1-yl}-2,2-diphenylethan-1-one fumarate, which as a contaminant comprises less than 0.1%, preferably less than 0.01% of at least one of the individual contaminants (VU1-VU11).

With conventional purification processes, such as chromatography, high-pressure liquid chromatography (HPLC), ion exchangers, etc., rac-1-{4-[2-hydroxy-3-(5-quinolyloxy)-propyl]-piperazin-1-yl}-2,2-diphenylethan-1-one fumarate cannot be produced in the purity according to the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 103 21 255.8, filed May 6, 2003, and U.S. Provisional Application Ser. No. 60/469,008, filed May 9, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. rac-1-{4-[2-Hydroxy-3-(5-quinolyloxy)propyl]-piperazin-1-yl}-2,2-diphenylethan-1-one fumarate, having a purity of more than 98.54%.
2. rac-1-{4-[2-Hydroxy-3-(5-quinolyloxy)propyl]-piperazin-1-yl}-2,2-diphenylethan-1-one fumarate, having a purity of at least 98.55.
3. rac-1-{4-[2-Hydroxy-3-(5-quinolyloxy)propyl]-piperazin-1-yl}-2,2-diphenylethan-1-one fumarate, having a purity of at least 99.55%.
4. rac-1-{4-[2-Hydroxy-3-(5-quinolyloxy)propyl]-1-piperazin-1-yl}-2,2-diphenylethan-1-one fumarate, having a purity of at least 99.65%.
5. rac-1-{4-[2-Hydroxy-3-(5-quinolylox)propyl]-piperazin-1-yl}-2,2-diphenylethan-1-one fumarate, having a purity of at least 99.84%.
6. rac-1-{4-[2-Hydroxy-3-(5-quinolyloxy)propyl]-piperazin-1-yl}-2,2-diphenylethan-1-one fumarate according to claim 1 in an amount of more than 1000 g.
7. rac-1-{4-[2-Hydroxy-3-(5-quinolyloxy)-propyl]-piperazin-1-yl}-2,2-diphenylethan-1-one fumarate according to claim 1, which contains less than 0.1% of

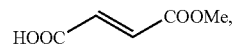

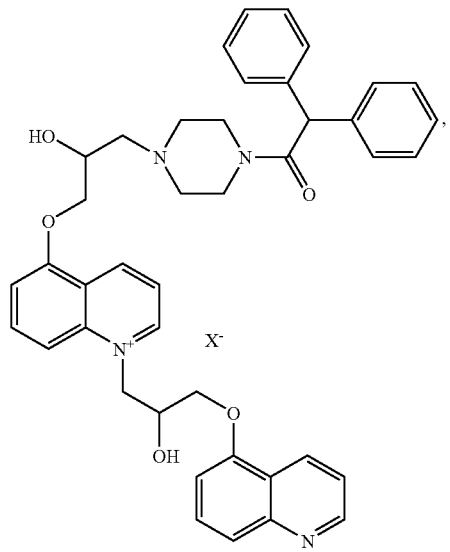

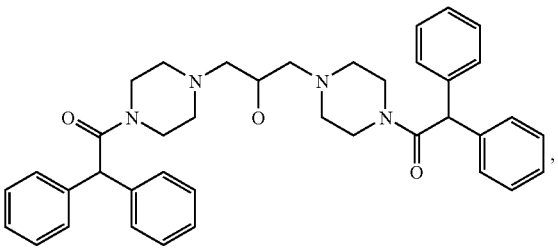

-continued
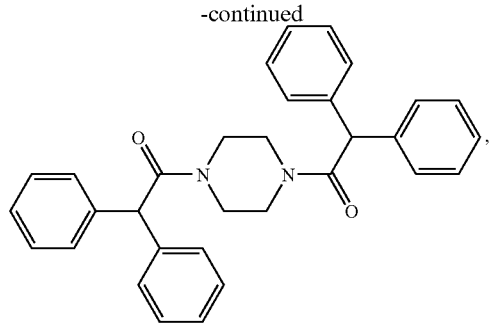
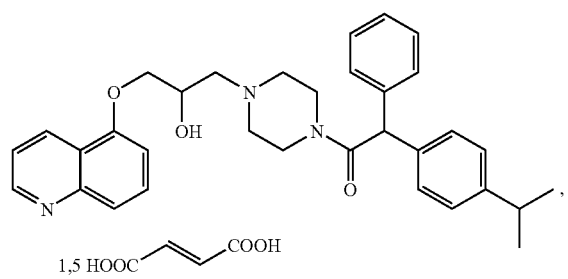
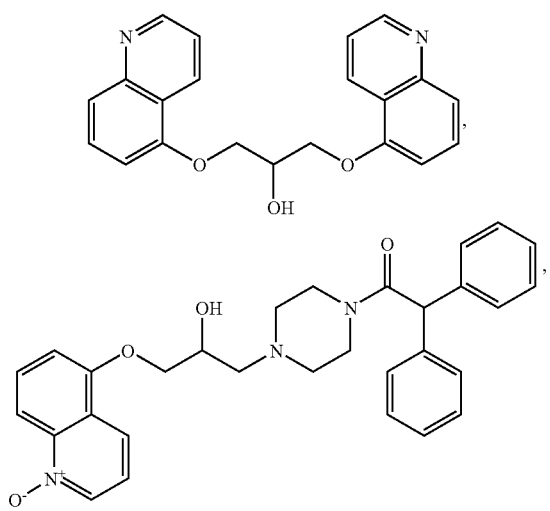
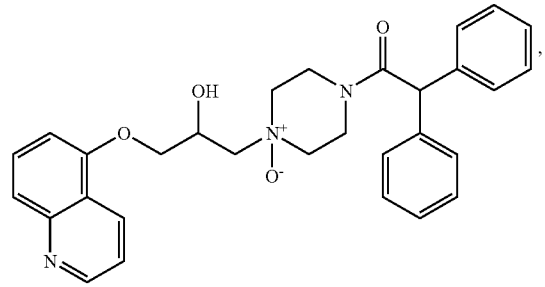
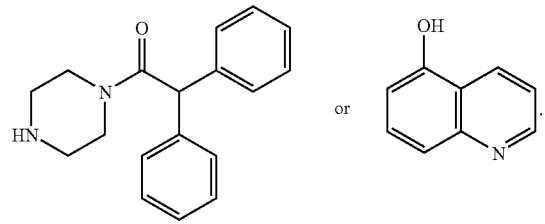
8. rac-1-{4-[2-Hydroxy-3-(5-quinolyloxy)-propyl]-piperazin-1-yl}-2,2-diphenylethan-1-one fumarate according to claim 1, which contains less than 0.01% of
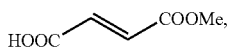
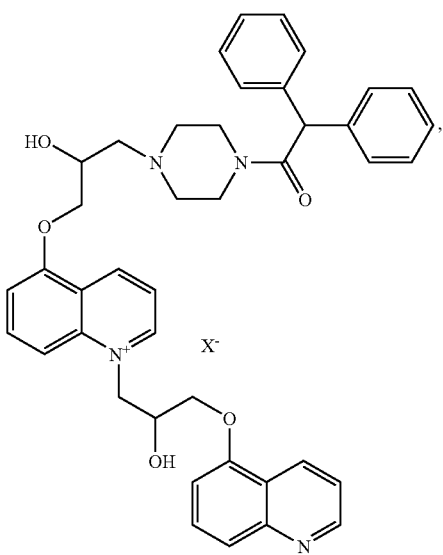
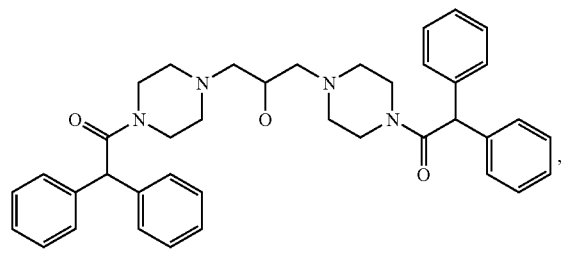
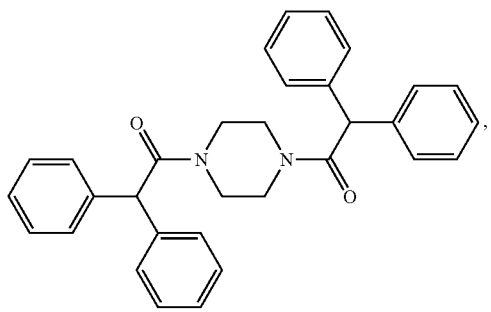
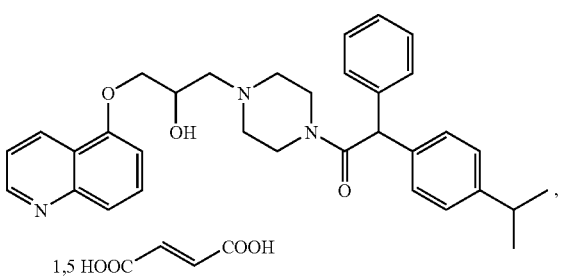

c) 1,1'-piperazine-1,4-diyl)bis(2,2-diphenylethan-1-one),
d)

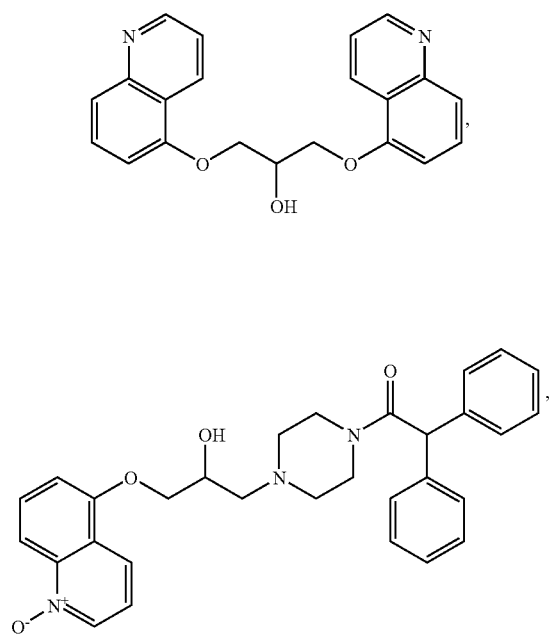

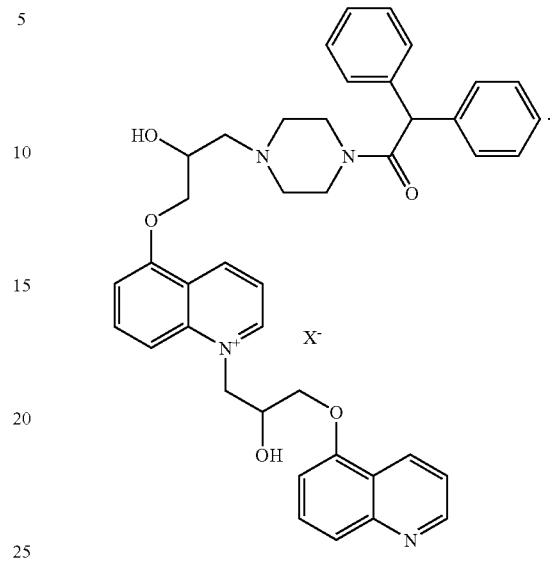

10. rac-1-{4-[2-Hydroxy-3-(5-quinolyloxy)propyl]-piperazin-1-yl}-2,2-diphenylethan-1-one fumarate, being a purity of at least 99.89%.

11. rac-1-{4-[2-Hydroxy-3-(5-quinolyloxy)propyl]-piperazin-1-yl}-2,2-diphenylethan-1-one fumarate, being a purity of at least 99.55% and which contains less than 0.1% of

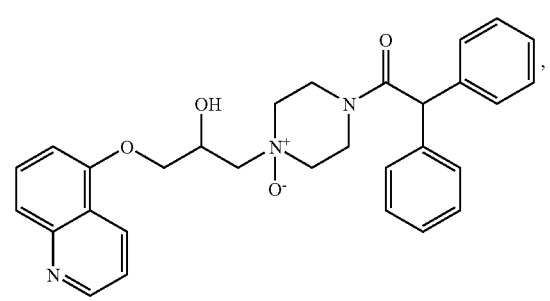

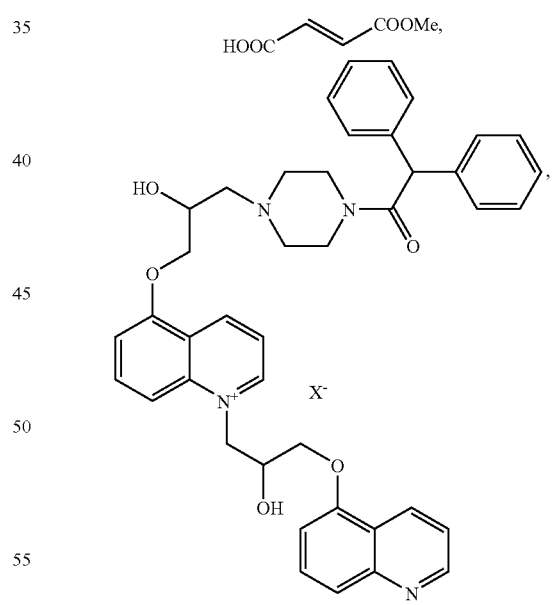

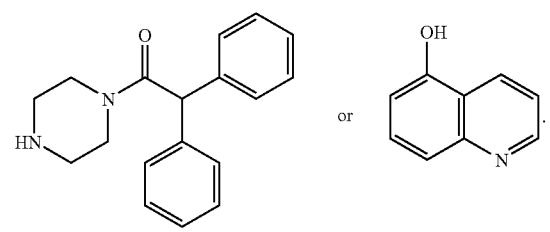

9. rac-1-{4-[2-hydroxy-3-(5-quinolyloxy)propyl]-piperazin-1-yl}-2,2-diphenylethan-1-one fumarate which does not contain a detectable amount of any of a)-d):

a) methyl hydrogen fumarate,
b) rac-1,1'-[2-hydoxypropane-1,3-diylbis(piperazine 1,4-diyl)]bis(2,2-diphenylethan-1-one),

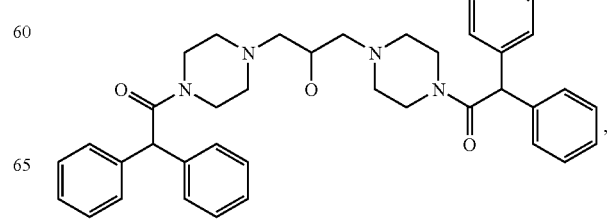

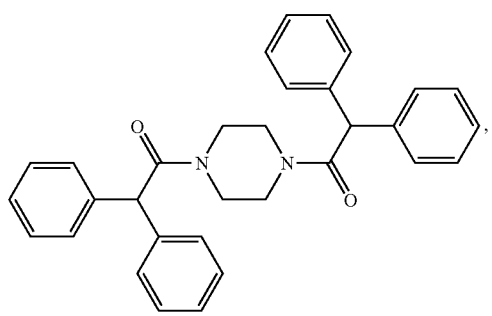,

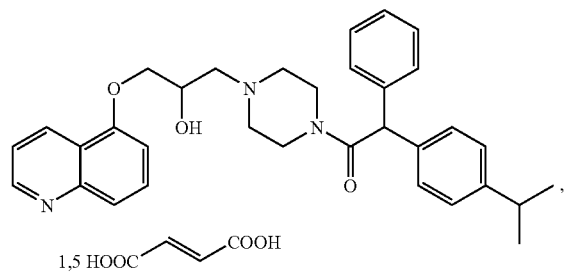

1,5 HOOC⁀COOH

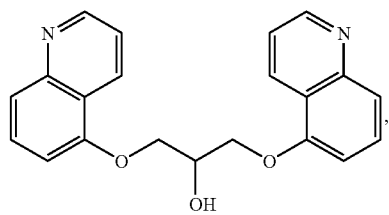,

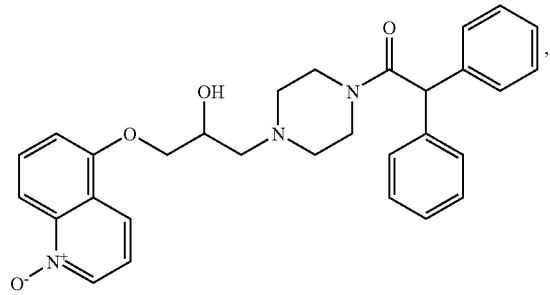,

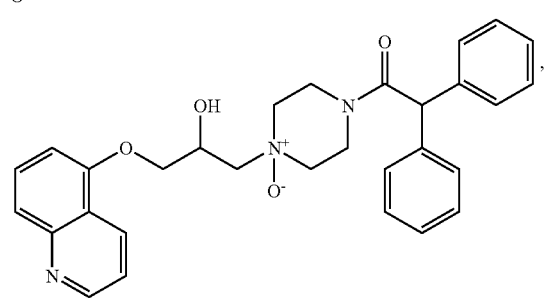

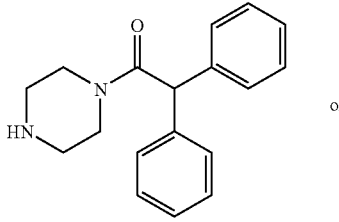    or    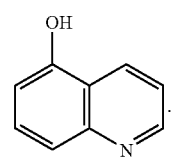.

12. A process for the production of high-purity rac-1-{4-[2-hydroxy-3-(5-quinolyloxy)propyl]-piperazin-1-yl}-2,2-diphenylethan-1-one fumarate, comprising reacting
  a) an epoxytosylate of structure I

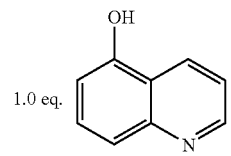 (I)

with
  b) 5-hydroxyquinoline (II)

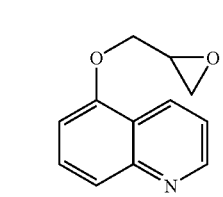 (II)

1.0 eq.

and cesium carbonate in a suitable solvent and at a temperature 35-60° C. to form the 5-(2,3-epoxypropoxy)-quinoline of formula III

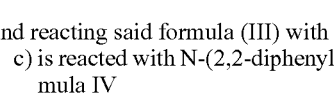 (III)

and reacting said formula (III) with
  c) is reacted with N-(2,2-diphenylacetyl)piperazine of formula IV

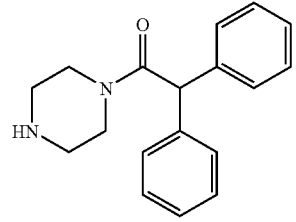 (IV)

in a solvent and at a suitable temperature 35-60° C. with the subsequent addition of solid fumaric acid to form crude rac-1-{4-[2-hydroxy-3-(5-quinolyloxy)propyl]-piperazin-1-yl}-2,2-diphenylethan-1-one fumarate of formula V

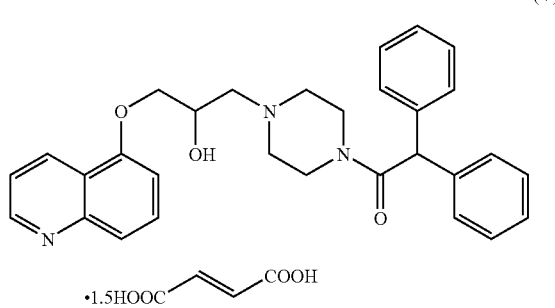

and then
d) the thus formed crude rac-1-{4-[2-hydroxy-3-(5-quinolyloxy)propyl]-piperazin-1-yl}-2,2-diphenylethan-1-one fumarate (V) is isolated and is dissolved in a solvent mixture that consists of methanol and methylene chloride, is treated with activated carbon, and then is filtered through a pressure filter with silica gel as a column material, and the thus obtained pure rac-1-{4-[2-hydroxy-3-(5-quinolyloxy)propyl]-piperazin-1-yl}-2,2-diphenylethan-1-one fumarate (V) is crystallized from a suitable alcohol.

13. A process according to claim 12, wherein acetone is used as a solvent.

14. A process according to claim 12, wherein the amount of silica gel is 3× the amount relative to the starting material.

15. A process according to claim 12, wherein the temperature in the crystallization in process stage (d) is 0° C.

* * * * *